United States Patent [19]

Michel et al.

[11] 4,131,547

[45] Dec. 26, 1978

[54] REFILLABLE COLUMN FOR CHROMATOGRAPHY AT ELEVATED PRESSURE

[75] Inventors: Karl H. Michel, Indianapolis; Robert F. Miller, Danville, both of Ind.

[73] Assignee: Eli Lilly and Company, Indianapolis, Ind.

[21] Appl. No.: 847,872

[22] Filed: Nov. 2, 1977

[51] Int. Cl.² ................................................ B01D 15/08
[52] U.S. Cl. ................................. 210/198 C; 210/232; 55/386
[58] Field of Search .................. 210/198 C, 31 C, 232; 55/386

[56] References Cited

U.S. PATENT DOCUMENTS

| 3,440,864 | 4/1969 | Blume | 210/198 C |
| 3,800,956 | 4/1974 | Nishizawa | 210/198 C |
| 3,904,527 | 9/1975 | Wilhelmson et al. | 210/198 C |
| 4,026,803 | 5/1977 | Abrahams et al. | 210/198 C |

*Primary Examiner*—John Adee
*Attorney, Agent, or Firm*—Ralph W. Ernsberger; Arthur R. Whale

[57] ABSTRACT

A refillable column for chromatography at elevated pressure is described comprised of a cylinder connected on both ends to a coupling having internal threads and an annular shoulder at the internal terminus of the threads. A plug having external threads is disposed in said coupling and sealed against the shoulder of the coupling. An axial hole communicates between the top and bottom of the plug. The column can be packed, emptied and repacked repeatedly.

8 Claims, 4 Drawing Figures

REFILLABLE COLUMN FOR CHROMATOGRAPHY AT ELEVATED PRESSURE

BACKGROUND OF THE INVENTION

Field of the Invention

This invention relates to a novel refillable column for chromatography at elevated pressure. More specifically, this invention comprises a device which can be repeatedly packed with a chromatographic material, emptied of such material when it is exhausted, or it is desired to employ a different material, and repacked with a fresh adsorbent by one of ordinary skill in the chromatographic art.

Prior Art

The process known as chromatography is old in the chemistry art. It is a means for separating chemical compounds, especially closely related ones, by allowing a solution of a mixture to seep through, or along, an adsorbent medium so that each compound becomes adsorbed in a separate layer, section, or portion of the adsorbent.

The chromatographic art has evolved steadily and, at times, dramatically from the early process known as open column chromatography to the highly sophisticated and useful chromatographic processes at elevated pressure commonly utilized today. Chromatography under pressure aids in the definitive separation of minute quantities of very closely related chemical compounds. In some instances pressure as great, or greater, than 100 atmospheres are employed in the process. For example, the analysis of blood to identify metabolites of physiologically active agents, which may be present in quantities measured in parts per billion, is often carried out at pressures of 1500 to 2000 psig, or higher.

A large number of highly refined adsorbents are available for use in high pressure chromatography. One, and not infrequently, a plurality of adsorbents is packed into a column providing a bed of adsorbent material having a length, or depth, several times greater than its cross-section (generally, diameter). The fluid mixture (solution) of the compounds desired to be separated is slowly percolated through the adsorbent bed. The pressure on the adsorbent bed can range from one to many atmospheres. The pressure can be varied by applying pressure, as with a pump, at the inlet to the column and restricting the rate of flow at the outlet from the column.

All sorts and varieties of columns for chromatography at elevated pressure, both packed with adsorbent and unpacked, are commercially available. Many of the pre-packed columns are not reuseable. Once the adsorbent has been exhausted (or poisoned) the column is no longer useful and must be replaced. Moreover, when a different adsorbent is desired, or needed, an entirely new column must be employed.

Some of the unpacked columns available commerically which can be packed by the user become single application columns once they are packed because they cannot be emptied and repacked because of their design.

Some of the refillable columns for chromatography at elevated pressure which are available are so designed that skilled hands are required to achieve an effective seal after the column has been repacked. Consequently the emptying and repacking of such columns is slow, cumbersome and expensive because of the level of skill required to satisfactorily accomplish the refilling operation.

Accordingly, it is an objective of this invention to provide a refillable column for chromatography at elevated pressure that can be readily emptied, repacked with the same or different adsorbent and resealed positively against pressure leaks with a minimum of time and skill.

SUMMARY

Now it has been discovered that a positively resealable refillable column for chromatography at elevated pressure can be comprised of a cylinder having a length to diameter ratio of 2:1 or more connected at each end to a coupling having internal threads and an annular shoulder at the internal terminus of the threads with a plug having external threads mated to the internal threads of the coupling disposed therein, said plug also having a depending extension adapted to contact the annular shoulder of the coupling achieving a seal therewith and an axial hole communicating between the bottom and top of the plug.

DESCRIPTION OF THE PREFERRED EMBODIMENTS

In the following detailed description of the embodiments of this invention, reference is made to the accompanying drawings.

One embodiment of the instant invention is a refillable column for chromatography at elevated pressure depicted in FIGS. 1–4. Such a device is comprised of: (a) a cylinder having a first and a second end with a length exceeding the diameter by a factor of 2 or more. Such a cylinder is connected at each end to a coupling having internal threads, preferably machine, of an inside diameter greater than that of said cylinder at the point of connection between said coupling and said cylinder and additionally having an annular shoulder disposed at the internal terminus of said threads. (b) A resilient plug having external threads, preferably machine, adapted to mate with the internal threads of the coupling is disposed therein. The plug has an inwardly tapered extension depending from said threads which is adapted to contact and cooperate with the annular shoulder of said coupling and form a seal therewith. The extension also has an inwardly and upwardly tapered bottom. The plug also has an axial bore with internal threads, preferably machine, disposed in the end opposite said extension and an axially disposed hole communicating between the bottom of said bore and the bottom of said extension. And, (c) a bushing having external threads, preferably machine, adapted to engage the internal threads of said bore is disposed therein. The bushing has an axial hole communicating between the top thereof and the axial hole in said plug. A tubular extension of said axial hole adapted to receive a flexible tube is connected to the top of said bushing.

Figure 1:
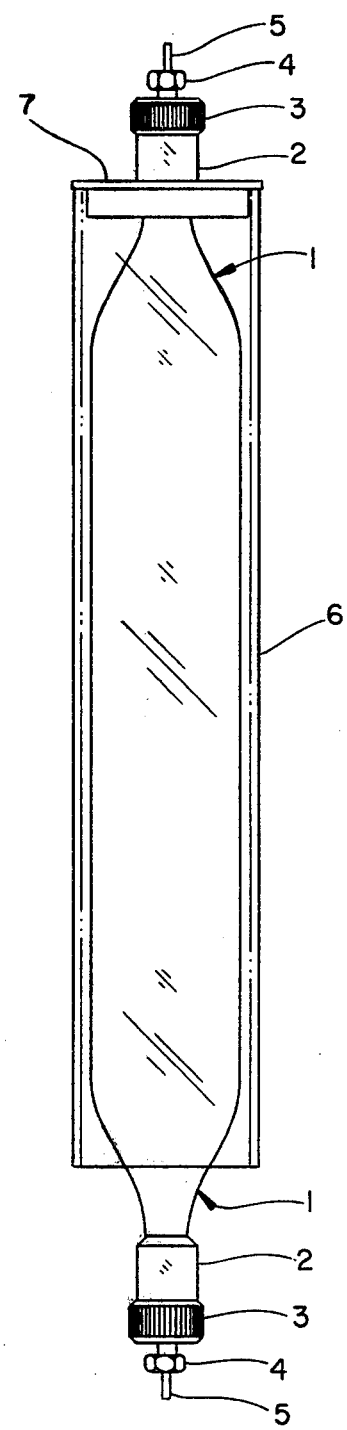
FIG. 1 is side elevation view of the refillable column for chromatography at elevated pressure of the instant invention with a safety shroud attached.

Referring to FIG. 1, there is seen a refillable column for chromatography at elevated pressure of this invention with a safety shroud 6 in place. The safety shroud constitutes no part of the instant invention and will not be discussed further. Those skilled in the art recognize the purpose such a shroud 6 serves.

The cylinder which holds the chromatographic material is shown as 1. In this rendering the cylinder is shown as having a body several times the diameter of the couplings 2 connected to both ends thereof. In this case the cylinder tapers gradually from the body thereof into the connections with the couplings 2. In most cases the body of the cylinder 1 will have a diameter greater than the diameter of the couplings 2. This is so because the rate of flow through the chromatographic material is relatively slow and does not require a large inlet and outlet to accomodate the fluid flow. However, the cylinder 1 need not be greater in diameter than the couplings 2. But there is generally no useful purpose served by having a cylinder of a lesser diameter than the couplings because the volume of the column can be better controlled by adjusting the length to the diameter to achieve the volume desired to contain the quantity of chromatographic material needed for the separation of the various compound in the solution passing through the column. For all practical purpose the length of the cylinder should exceed the diameter by a factor of 2, or more.

Figure 2:
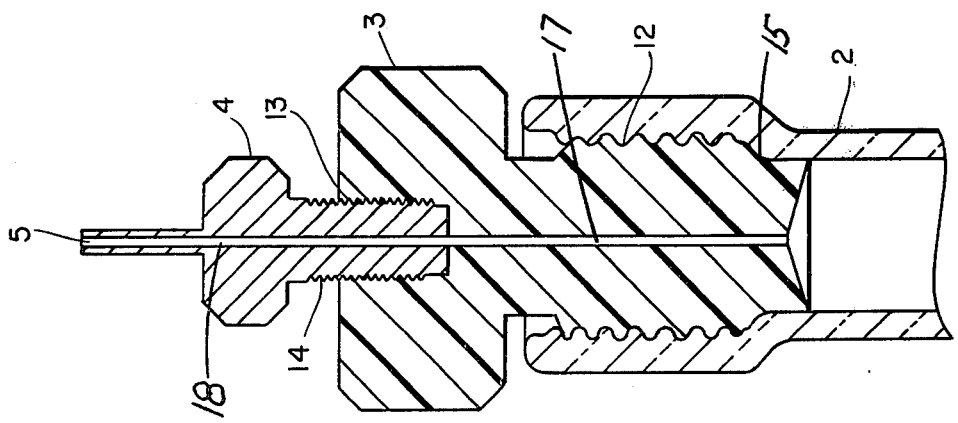
FIG. 2 is a cross-sectional view showing the resilient plug and bushing disposed in the coupling connected to the cylinder of the column.

At the bottom of FIG. 1 and in FIG. 2 it is shown that both the outside and inside diameters of the couplings 2 are greater than the cylinder 1. This is an essential element of the construction which is discussed more throughly later.

In FIG. 1 there is a knurled nut shown which is a part of resilient plug 3. The knurling is for convenience only in installing and removing plug 3 from coupling 2. A bushing 4 with a tubular extension 5 is shown disposed in plug 3. It is to be noted that in FIG. 1, both ends of the cylinder are identical. This is a convenient construction. But identical construction as to size is of no consequence in the invention. However, both ends of the cylinder do have couplings, plugs and bushings of similar construction so that the same condition obtain and the same purpose is achieved.

FIG. 2 clearly shows the crux of the instant invention. Coupling 2 has an annular shoulder 15 just above the point of connection with the cylinder. This annular shoulder 15 serves as a seat which is contacted by the extension 16 of plug 3 which depends below the external threads 8 shown in FIG. 3. The coupling 2 has internal threads 12 which mate with the external threads 8 of the plug 3. When plug 3 is disposed in coupling 2 and tightened down so that the extension 16 of plug 3 contacts the annular shoulder 15 of coupling 2 a pressure tight seal is formed.

Figure 3:
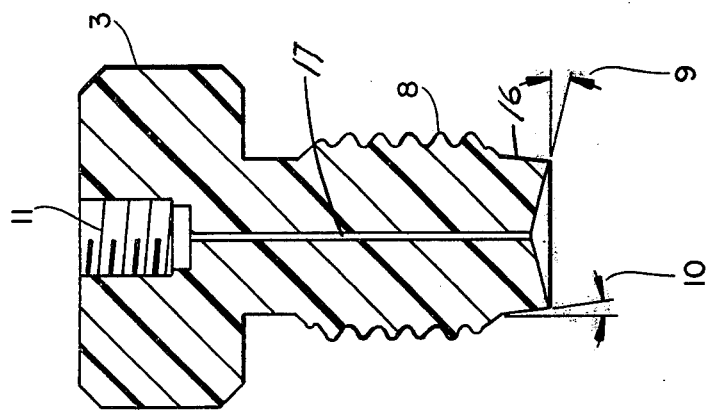
FIG. 3 is a cross-sectional view of the resilient plug disposed in the coupling shown in FIG. 2.

In order to obtain the pressure tight seal the angles 9 and 10 shown on plug 3 in FIG. 3 aid in effecting the seal. The extension 16 depending from the terminus of the external threads 8 or plug 3 is preferably tapered inwardly at an angle 10 of from about 1° to about 15°. This allows the extension 16 to clear the inside wall of the coupling below the annular shoulder 15 thereof and establish a firmly sealed contact therewith. The inwardly and upwardly tapers of the bottom of plug 3, angle 9, provides yield for the compression of the extension of plug 3 as the bottom is tightened against the annular shoulder 15 of coupling 2. Angle 9 should preferably be from about 5° to about 25° to achieve the needed yield. Those skilled in the art will recognize that the greater the diameter of the extension of plug 3 the greater the taper of angle 9, for a shallow angle 9 coupled with a substantial diameter will reduce the yield of the resident plug and make the establishment of a tight seal more difficult.

The bore 11 is shown clearly in FIG. 3. The axial hole 17 communicates between the bottom of plug 3 and the bottom of bore 11 is plug 3.

Bushing 4 is shown in FIG. 2 disposed in bore 11. The internal threads in bore 11 are shown as 13 and the external threads of bushing 4 are shown as 14. Extending upwardly from bushing 4 and communicating with axial hole 18 in bushing 4 is a tube 5 adopted to receive a flexible connection.

The complete assembly shown in FIG. 2 depicts the axial hole 17 in plug 3, the axial hole 18 in bushing 4 and the hole in tube 5 in alignment and communicating between an external inlet and the interior of the cylinder of the refillable column for chromatography at elevated pressure of this invention.

Figure 4:
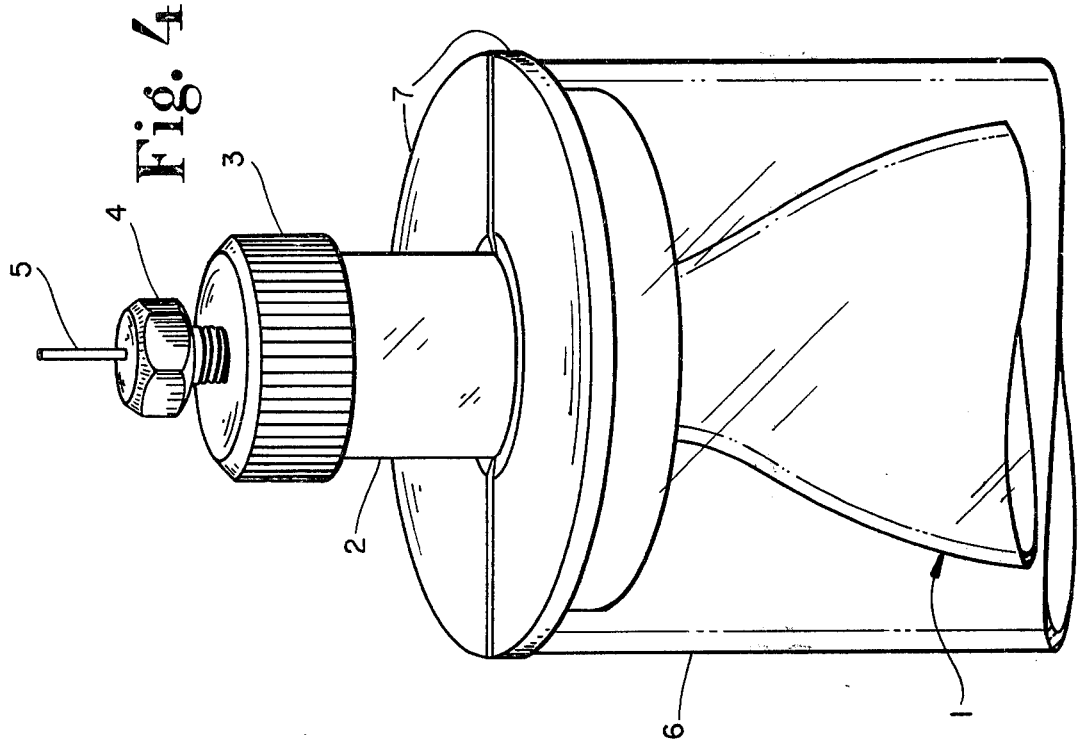
FIG. 4 is a cut away profile of the top portion of the column and safety shroud of FIG. 1.

FIG. 4 is a blown up section from FIG. 1 showing the top portion of the column 1 and shroud 6. A split collar 7 holds the shroud around column 1. The interior opening in the split collar reposes on the outside diameter of the annular collar of coupling 2 and the shroud 6 is held on the split collar 7 by an internal flange with an outside diameter slightly less than the inside diameter of the shroud. The shroud is clamped to a laboratory support to hold column 1 in a vertical altitude.

In another embodiment of this invention all of the elements are the same as those described above except that no bushing 4 is utilized and instead of a bore 11 in plug 3, the axial hole 17 therein is continued to the top thereof and communicates with a tubular extension such as 5 shown on bushing 4. Column 1 is connected to couplings 2 which in turn have modified plugs 3 disposed therein.

The benefit achieved by the refillable column for chromatography at elevated pressure of the instant invention lies in the fact that the column can be refilled repeatedly with a chromatographic material, such as finely ground attapulgite, silica gel, montmorrilnite, kaolin, and the like. There is no need to discard the entire column when the chromatographic material contained therein is exhausted. A tight seal is easily and routinely obtained after refilling.

Ordinarily, the cylinder will be a transparent material such as glass. This, however, is not a requirement. Other materials of construction can be utilized, such as polyacrylic, polymethacrylic, polycarbonate and other synthetic polymeric material. Generally, opaque metals are not preferred because there is no way to visually determine the zones of adsorbancy.

The refillable columns for chromatography at elevated pressure detailed above are prepared for use by placing in one end a filter material designed to hold the chromatographic material, such as glass wool, asbestos, felt, paper, and the like. Then a slurry of the desired chromatographic material is slowly introduced into the other end of column and as the vehicle drains from the open lower end of the column, the bed of chromatographic material is slowly built up until the desired quantity of material is contained in the column. The plugs, and bushings if they are used, are inserted in the couplings and tightened to effect a pressure tight seal. The bed of chromatographic material is then conditioned in a manner known to those skilled in the art and appropriate for the use to which the column is to be put. Such a refillable column for chromatography at elevated pressure is useful for running chromatographic separation at pressures from about 1 to about 400 psig depending on the diameter of the cylinder, the material of construction of the cylinder, and the other parts which constitute the column. Those skilled in the art will recognize the maximum safe pressure to which a particular sized column constructed of a particular material can be operated.

The resilient material from which the plugs can be made include such diverse polymeric substances as polytetrafluoroethane, polychlorofluoroethane, polyethylene, polypropylene, nylon, modified acrylic and methacrylic polymers, and the like. Preferred for its inertness is polytetrafluoroethane. However, those skilled in the art will recognize the degree of inertness required by the character of the chromatographic separation contemplated and can select other materials of equal utility where adequate chemical inertness is present.

The bushing can be constructed of any material suitable for withstanding the pressure employed, and the solvent system utilized. The plastic materials noted in the paragraph above as well as such metals as brass, monel, stainless steel, and the like can be used. Care must be exercised in installing the bushing in the resilient plug to effect a solid seal between the bottom of the bushing and the bottom of the bore in the plug.

The preferred construction of the coupling and the cylinder is of glass. When such a construction is utilized a coupling available in commerce can be connected to the cylinder of the column by drawing the end of the cylinder to the same outside diameter as that of the coupling and joining the two pieces together by a simple glass blowing procedure, a procedure well known to those skilled in the art.

What is claimed is:

1. A refillable column for chromatography at elevated pressure comprised of:
   (a) a cylinder having a first and a second end with a length exceeding the diameter by a factor of 2 or more, said cylinder being connected at each end to a coupling having internal threads of an inside diameter greater than the inside diameter of said cylinder at the point of connection between said coupling and said cylinder and an annular shoulder disposed at the internal terminus of said thread;
   (b) a resilient plug having external threads adapted to mate with said internal threads of said coupling disposed therein, said plug having an inwardly tapered extension depending from said threads adapted to contact and cooperate with the annular shoulder of said coupling forming a seal therewith, said extension also having an inwardly and upwardly tapered bottom, said plug also having an axial bore with internal threads disposed in the end opposite said extension and an axially disposed hole communicating between the bottom of said bore and the bottom of said extension of said plug; and
   (c) a bushing having external threads adapted to engage the internal threads of said bore and disposed therein, said bushing also having an axial hole communicating between the top thereof and the axial hole in said plug with a tubular extension from the top of said hole adapted to receive a flexible tube connection therewith.

2. The refillable column for chromatography at elevated pressure of claim 1 wherein the ratio of the diameter of said cylinder to the diameter of said coupling is 1:1 or more.

3. The refillable column for chromatography at elevated pressure of claim 1 wherein the extension of said resilient plug is tapered inwardly at an angle of from about 1° to about 15°.

4. The refillable column for chromatography at elevated pressure of claim 1 wherein the bottom of the extension of said plug is tapered inwardly and upwardly toward said axially disposed hole at an angle of from about 5° to about 25°.

5. A refillable column for chromatography at elevated pressure comprised of:
   (a) a cylinder having a first and a second end with the length exceeding the diameter by a factor of 2, or more, said cylinder being connected at each end to a coupling having internal threads of an inside diameter greater than the inside of said cylinder at the point of connection between said coupling and said cylinder and an annular shoulder disposed at the internal terminus of said threads; and
   (b) a resilient plug having external threads adapted to mate with said internal threads of said coupling disposed therein, said plug having an inwardly tapered extension depending from said threads adapted to contact and cooperate with the annular shoulder of said coupling, said extension also having a bottom tapering inwardly and upwardly to the center thereof whereas there is an axial hole extending upwardly and communicating with the top of said plug, said plug also having a tubular extension of said axial hole attached to the top thereof adapted for connecting with a flexible tube.

6. The refillable column for chromatography at elevated pressure of claim 5 wherein the ratio of the diameter of said cylinder to the diameter of said couplings is 1:1, or more.

7. The refillable column for chromatography at elevated pressure of claim 5 wherein the extension of said resilient plug is tapered inwardly at an angle of from about 1° to about 15°.

8. The refillable column for chromatography at elevated pressure of claim 5 wherein the bottom of the extension of said plug is tapered inwardly and upwardly toward said axially disposed hole at an angle of from about 5° to about 25°.

* * * * *